(12) United States Patent
Gordon et al.

(10) Patent No.: US 7,737,290 B2
(45) Date of Patent: Jun. 15, 2010

(54) ATOMIC LAYER DEPOSITION USING METAL AMIDINATES

(75) Inventors: Roy Gerald Gordon, Cambridge, MA (US); Booyong S. Lim, Lexington, MA (US)

(73) Assignee: President and Fellows of Harvard University, Cambridge, MA (US)

( * ) Notice: Subject to any disclaimer, the term of this patent is extended or adjusted under 35 U.S.C. 154(b) by 0 days.

(21) Appl. No.: 12/496,499

(22) Filed: Jul. 1, 2009

(65) Prior Publication Data

US 2010/0092667 A1  Apr. 15, 2010

Related U.S. Application Data

(62) Division of application No. 10/534,687, filed as application No. PCT/US03/36568 on Nov. 14, 2003, now Pat. No. 7,557,229.

(60) Provisional application No. 60/426,975, filed on Nov. 15, 2002, provisional application No. 60/463,365, filed on Apr. 16, 2003.

(51) Int. Cl.
*C07F 15/00* (2006.01)
*C07F 9/00* (2006.01)
*C07F 7/00* (2006.01)
*C23C 16/00* (2006.01)

(52) U.S. Cl. .............................. 556/138; 556/1; 556/51; 556/118; 556/137; 534/15; 427/255.19; 427/255.394

(58) Field of Classification Search ............... 556/1, 556/51, 118, 137, 138; 534/15; 427/255.19, 427/255.394
See application file for complete search history.

(56) References Cited

U.S. PATENT DOCUMENTS

| 5,085,731 | A | 2/1992 | Norman et al. |
| 5,098,516 | A | 3/1992 | Norman et al. |
| 5,144,049 | A | 9/1992 | Norman et al. |
| 5,204,314 | A | 4/1993 | Kirlin et al. |
| 5,225,561 | A | 7/1993 | Kirlin et al. |
| 5,235,078 | A | 8/1993 | Pohl et al. |

(Continued)

FOREIGN PATENT DOCUMENTS

DE   4039449   6/1992

(Continued)

OTHER PUBLICATIONS

Barker et al., "The Coordination Chemistry of the Amidine Ligand", Coordination Reviews, vol. 133, pp. 219-300, 1994.

(Continued)

*Primary Examiner*—Porfirio Nazario Gonzalez
(74) *Attorney, Agent, or Firm*—Wilmer, Cutler, Pickering, Hale & Dorr, LLP

(57) ABSTRACT

Metal films are deposited with uniform thickness and excellent step coverage. Copper metal films were deposited on heated substrates by the reaction of alternating doses of copper(I) NN'-diisopropylacetamidinate vapor and hydrogen gas. Cobalt metal films were deposited on heated substrates be the reaction of alternating doses of cobalt(II) bis(N,N'-diisopropylacetamidinate) vapor and hydrogen gas. Nitrides and oxides of these metals can be formed by replacing the hydrogen with ammonia or water vapor, respectively. The films have very uniform thickness and excellent step coverage in narrow holes. Suitable applications include electrical interconnects in microelectronics and magnetoresistant layers in magnetic information storage devices.

27 Claims, 7 Drawing Sheets

U.S. PATENT DOCUMENTS

| | | | |
|---|---|---|---|
| 5,280,012 | A | 1/1994 | Kirlin et al. |
| 5,322,712 | A | 6/1994 | Norman et al. |
| 5,362,328 | A | 11/1994 | Gardiner et al. |
| 5,453,494 | A | 9/1995 | Kirlin et al. |
| 5,502,128 | A | 3/1996 | Flores et al. |
| 5,536,323 | A | 7/1996 | Kirlin et al. |
| 5,711,816 | A | 1/1998 | Kirlin et al. |
| 5,820,664 | A | 10/1998 | Gardiner et al. |
| 5,834,058 | A | 11/1998 | Wallbridge et al. |
| 5,919,522 | A | 7/1999 | Baum et al. |
| 5,932,363 | A | 8/1999 | Hu et al. |
| 6,110,529 | A | 8/2000 | Gardiner et al. |
| 6,211,090 | B1 | 4/2001 | Durlam et al. |
| 6,294,836 | B1 | 9/2001 | Paranjpe et al. |
| 6,337,148 | B1 | 1/2002 | Xu et al. |
| 6,417,369 | B1 | 7/2002 | Xu et al. |
| 6,440,202 | B1 | 8/2002 | Xu et al. |
| 6,444,263 | B1 | 9/2002 | Paranjpe et al. |
| 6,639,080 | B2 | 10/2003 | Xu et al. |
| 6,818,783 | B2 | 11/2004 | Norman et al. |
| 2002/0081381 | A1 | 6/2002 | DelaRosa et al. |
| 2002/0132375 | A1 | 9/2002 | Doan et al. |
| 2002/0173054 | A1 | 11/2002 | Kim |
| 2004/0175502 | A1 | 9/2004 | Senzaki |
| 2005/0042372 | A1 | 2/2005 | Denk et al. |
| 2005/0214458 | A1 | 9/2005 | Meiere |
| 2005/0281952 | A1 | 12/2005 | Xu et al. |
| 2006/0062910 | A1 | 3/2006 | Meiere |
| 2006/0177577 | A1 | 8/2006 | Thompson |
| 2006/0193979 | A1 | 8/2006 | Meiere et al. |

FOREIGN PATENT DOCUMENTS

| | | |
|---|---|---|
| EP | 1 142 894 B1 | 10/2001 |
| GB | 2295392 A | 5/1996 |
| GB | 2295393 A | 5/1996 |
| JP | 200269088 | 11/1990 |
| WO | WO-91/08322 | 6/1991 |
| WO | WO-01/68948 A1 | 9/2001 |
| WO | WO-2004/046417 | 6/2004 |

OTHER PUBLICATIONS

Barker, j. et al., N,N-Unsubstituted amidinato metallacycle complexes of Group 13 metal alkyls: the crystal structure of trimeric [{Me$_2$Al(υ-HNCPhNH))$_3$], Journal of Organometallic Chemistry, vol. 586, pp. 138-144, 1999.

Berno et al. "Dinitrogen Fixation versus Metal-Metal Bond Formation int he Chemistry of Vanadium (II) Amidinates" *J. Am. Chem. Soc.* 1994, 116 (7417-7418).

Booyong, S. et al., "Atomic Layer Deposition of Transition of Metals", Nature Publishing Group, Department of Chemistry and Chemical Biology, Harvard University, pp. 749-754, 2003.

Booyong, S. et al., "Synthesis and Characterization of Volatile, Thermally Stable, Reactive Transition Metal Amidinates", Inorganiz Chemistry, vol. 42, No. 24, pp. 7951-7958, 2003.

Cole, M., et al., "The Synthesis of a Sterically Hindered Samarium(II) bis(amidinate) and conversion to its homoleptic trivalent congener," Chemical Communications, 2005, pp. 2695-2697.

Coles, M.P. et al., "Synthesis and Structures of Mono- and Bis(amidinate) Complexes of Aluminum," Organometallics, vol. 16, 1997, pp. 5183-5194.

Cotton, F. A., et al., J. Am. Chem. Soc., vol. 110, pp. 7077-7083, 1988.

Dias, H. V. Rasika et al., "Coinage Metal Complexes of 3,5-bis(trifluoromethyl)pyrazolate Ligand: Synthesis and Characterization of {[3,5-(CF3)2Pz]Cu}3 and {3,5(CF3)2Pz]3", Journal of Fluorine Chemistry 2000, vol. 103, pp. 163-169.

Edelmann, "N-Silylated Benzamidines: Versatile Building Blocks in Main Group and Coordination Chemistry", vol. 137, pp. 403-481, (1994).

Fix, et al., "Chemical Vapor Deposition of Titanium, Zirconium, and Hafnium Nitride Thin Films", American Chemical Society, vol. 3(6), pp. 1138-1148, 1991.

Hao et al, "Ligand Steric Bulk: A Neglected Favor in the Formation of Cr-Cr Sypershort Contacts", Inorganica Chimica Acta, vol. 213, pp. 65-74, (1996).

Hao et al. "The role of ligand steric hindrance in determining the stability of very short V-V contacts. Preparation and characterization of a series of V(II) and V(III) amidinates" *Inorganica Chimica Act* 244 (1996) 37-49.

International Search Report from PCT/US2007/014768, mailed Nov. 11, 2007, 4 pages.

International Search Report from the European Patent Office for PCT/US03/36568, mailing date Jan. 17, 2005, 7 pages.

Kilner, M. et al., Polyhedron, vol. 2, No. 12, pp. 1379-1388, 1983.

Li, Z. et al., Synthesis and Characterization of Copper(I) Amidinates as Precursors for Atomic Layer Deposition (ALD) of Copper Metal, *Inorganic Chemistry*, vol. 44, pp. 1728-1735, 2005.

Lim et al. "Synthesis and Characterization of Volatile, Thermally Stable, Reactive Transition Metal Amidinates" *Inorganic Chemistriy* 2003, 42 (7951-7958).

Lim, B. et al., "Atomic layer deposition of transition metals", Nature Materials, vol. 2, pp. 749-754, Nov. 2003.

Martensson, P. et al., "Atomic Layer Epitaxy of Copper", J. Electrochem. Soc., vol. 145, pp. 2926-2931, Aug. 1998.

Official Action issued by the European Patent Office on Jan. 25, 2006 in connection with European Patent Application No. 03 783.541.0.

Sadique et al., "Monomeric and Dimeric Amidinate Complexes of Magnesium", Inorg. Chem., vol. 40, pp. 6349-6355, 2001.

Sadique, AR et al., "A Weak, Short Metal-Metal Bond in a Chromium (II) Amidinate Complex", J. Am. Chem. Soc., vol. 125, pp. 7774-7775, 2003.

Schmidt, J. A.R. et al., "First-row transition metal complexes of sterically-hindered amidinates", J. Chem. Soc., Dalton Trans., pp. 3454-3461, 2002.

Shibayama, K. et al., "Living Polymerization of Carbodiimides Initiated by Copper(I) and Copper (II) Amidinate Complexes" Macromolecules, vol. 30, pp. 3159-3163, 1997.

Vendemiati et al., "Paramagnetic Bis(amidinate) Iron (II) Complexes and their Diamagnetic Dicarbonyl Derivatives", Eur. J. Inorg. Chem., pp. 707-711, 2001.

Zhengwen, L. et al., "Synthesis and Characterization of Copper(I) Amidinates as Precursors for Atomic Layer Deposition (ALD) of Copper Metal", Inorganic Chemistry, vol. 44, No. 6, pp. 1728-1735, 2005.

ATOMIC LAYER DEPOSITION USING METAL AMIDINATES

This application claims the benefit, under 35 U.S.C. §121, of the earlier filing date of U.S. patent application Ser. No. 10/534,687, filed May 12, 2005; which is a U.S. National Stage Application of International Application No. PCT/US2003/036568, filed Nov. 14, 2003; which is an application claiming the benefit under 35 USC 119(e) of U.S. Provisional Patent Application No. 60/463,365 filed Apr. 16, 2003; which is an application claiming the benefit under 35 USC 119(e) of U.S. Provisional Patent Application No. 60/426,975 filed Nov. 15, 2002, all of which are incorporated herein by reference in their entirety.

BACKGROUND OF THE INVENTION

1. Field of the Invention

This invention relates to materials and processes for deposition of conformal films containing metals on solid substrates, and in particular, to films inc and iron metals or their oxides or nitrides. This invention may be applied to the fabrication of microelectronics devices.

2. Description of the Related Art

As the speed and functionality of semiconductor microelectronic devices are improved, new materials are needed. For example, materials with higher electrical conductivity are needed to form the wiring between transistors in integrated circuits. Copper has higher electrical conductivity and better stability against electro-migration than does aluminum. Therefore, copper is becoming more commonly used in silicon semiconductors. This trend is described in the International Technology Roadmap for Semiconductors, published on the Internet at http://public.itrs.net/Files/2001ITRS/Home.htm.

Copper interconnections must also be disposed conformally in structures, such as narrow holes, and the resulting films must have highly uniform thickness. If there are variations in thickness, the electrical conductivity of the copper in a trench or via is degraded because of increased electron scattering from the rough surface of the copper. Thus high-quality barrier/adhesion layers desirably have very smooth surfaces.

One method that is suitable for making smooth, conformal layers is "atomic layer deposition", or ALD (also known as atomic layer epitaxy). The ALD process deposits thin layers of solid materials using two or more different vapor phase precursors. The surface of a substrate onto which film is to be deposited is exposed to a dose of vapor from one precursor. Then any excess unreacted vapor from that precursor is pumped away. Next, a vapor dose of the second precursor is brought to the surface and allowed to react. This cycle of steps can be repeated to build up thicker films. One particularly important aspect of this process is that the ALD reactions are self-limiting, in that only a certain maximum thickness can form in each cycle, after which no further deposition occurs during that cycle, even if excess reactant is available. Because of this self-limiting character, ALD reactions produce coatings with highly uniform thicknesses. Uniformity of ALD film thicknesses extends not only over flat substrate surfaces, but also into narrow holes and trenches. This ability of ALD to make conformal films is called "good step coverage."

ALD of copper has been demonstrated from the copper precursor Cu(II)-2,2,6,6-tetramethyl-3,5-heptanedionate by P. Martensson and J. O. Carlsson in the Journal of the Electrochemical Society, volume 145, pages 2926-2931 (1998). Unfortunately, copper from this ALD process only grows on pre-existing platinum surfaces, and does not nucleate or adhere to most other surfaces in the temperature range (<200° C.) in which there is a true self-limiting ALD process. Other reactions have been suggested for ALD of copper, but no data have been published to demonstrate that the proposed surface reactions are actually self-limiting. Therefore it would be highly advantageous to have an ALD process for copper that nucleates and adheres to surfaces other than platinum.

U.S. Pat. No. 6,294,836 reports improvement in the adhesion of copper by use of a "glue" layer of cobalt between the copper and a substrate. However, known chemical vapor deposition (CVD) techniques for depositing cobalt have poor step coverage, giving only 20% thickness at the bottom of a hole with aspect ratio 5:1, according to U.S. Pat. No. 6,444,263. ALD of cobalt has been claimed in US Patent Application No. 2002/0081381 for the reaction of cobalt bis(acetylacetonate) [$Co(acac)_2$] with hydrogen, but no step coverage data were given and growth was seen only on preexisting iridium surfaces. US Patent Application No. 2002/0081381 also claims non-selective growth of cobalt by the reaction of $Co(acac)_2$ with silane, but this cobalt may be contaminated with silicon. Thus it would be advantageous to have a deposition process for pure cobalt having high step coverage.

Thin layers of copper and cobalt are also used to form magnetoresistant write and read heads for magnetic information storage. These layers need to have very uniform thicknesses and very few defects or pinholes. While successful commercial processes exist for making these devices, it would be advantageous to have deposition processes for copper and cobalt that produced layers with more uniform thickness and fewer defects.

Advanced designs for magnetic memory integrated with microelectronic circuits (see, for example, US Patent Application No. 2002/0132375 and U.S. Pat. No. 6,211,090) call for highly uniform and conformal layers of metals (particularly Fe, Co, Ni, Cu, Ru, Mn) with tightly controlled thickness and sharp interfaces. There are no known methods for depositing these metal layers with the required conformality and control of thickness.

SUMMARY OF THE INVENTION

One aspect of the present invention includes a process for depositing films comprising metals such as copper, cobalt, nickel, iron, ruthenium, manganese, chromium, vanadium, niobium, tantalum, titanium or lanthanum using a volatile metal amidinate compound. The films have uniform, conformal thicknesses and smooth surfaces.

An advantage of this process is its ability to form metal-containing coatings with extremely uniform thickness.

A related aspect of the present invention is the deposition of metal-containing coatings under conditions that produce good adhesion between substrates and the deposited coating.

An advantage of the process is that it permits deposition of metal-containing coatings with extremely smooth surfaces.

An additional advantage of the process is the vapor deposition of highly uniform metal-containing coatings is accomplished over a range of conditions such as concentrations of reactants and position of the substrate inside the reactor.

Another advantage of the invention is its ability to make conformal metal-containing coatings of over substrates with narrow holes, trenches or other structures. This ability is commonly known as "good step coverage."

Another aspect of the present invention is the preparation of metal-containing coatings that are substantially free of pin-holes or other mechanical defects.

Another advantage of the invention is the ability to deposit metal-containing coatings with high electrical conductivity.

Another advantage of the invention is the ability to deposit metal-containing coatings that adhere strongly to oxide substrates.

Another advantage of the invention includes the ability to coat substrates with metal-containing coatings at relatively low temperatures.

A further aspect of the invention includes a process for atomic layer deposition of metal-containing coatings without plasma damage to substrates.

One particular aspect of the present invention includes a process for depositing electrically conductive copper coatings for use as connectors in microelectronic devices.

Another particular aspect of the present invention includes a process for depositing cobalt coatings having useful magnetic properties.

An additional aspect of the invention is the deposition of a cobalt layer and then a copper layer on a diffusion barrier (such as TiN, TaN or WN) in a microelectronic interconnect structure.

A further aspect of the present invention includes a process for depositing cobalt/copper nanolaminate coatings having useful magneto-resistance properties.

In one aspect of the present invention, a thin film comprising a metal is prepared by exposing a heated substrate alternately to the vapor of one or more volatile metal amidinate compounds (M-AMD), and then to a reducing gas or vapor, to form a metal coating on the surface of the substrate. In one or more embodiments, the reducing gas includes hydrogen.

In one aspect of the invention, a thin film comprising a metal nitride is prepared by exposing a heated substrate alternately to the vapor of one or more volatile metal amidinate compounds (M-AMD), and then to a nitrogen-containing gas or vapor, to form a metal nitride coating on the surface of the substrate. In one or more embodiments, the nitrogen-containing gas includes ammonia.

In another aspect of the invention, a thin film comprising a metal oxide is prepared by exposing a heated substrate alternately to the vapor of one or more volatile metal amidinate compounds (M-AMD), and then to an oxygen-containing gas or vapor, to form a metal oxide coating on the surface of the substrate. In one or more embodiments, the oxygen-containing gas includes water.

In one or more embodiments, the volatile metal amidinate compound is a metal amidinate compound having a formula selected from the group consisting of M(I)AMD, M(II)AMD$_2$ and M(III)AMD$_3$ and oligomers thereof, where M is a metal and AMD is an amidinate moiety.

In one aspect of the invention vapors of a volatile copper compound are reacted alternately with hydrogen gas at a surface to produce thin layers of copper metal on the surface. Particularly suitable copper compounds are chosen from the class of copper(I) amidinates.

In another aspect of the invention vapors of a volatile cobalt compound are reacted alternately with hydrogen gas at a surface to produce thin layers of cobalt metal on the surface. Particularly suitable cobalt compounds are chosen from the class of cobalt(II) amidinates. Replacing the hydrogen gas in this process with ammonia gas can deposit cobalt nitride. Replacing the hydrogen gas in this process with water vapor can deposit cobalt oxide.

In other embodiments of the invention, amidinates of nickel, iron, ruthenium, manganese, chromium, vanadium, niobium, tantalum, titanium and lanthanum are used for vapor deposition of thin films comprising one or more of these metals.

In another aspect of the invention vapors of a volatile lanthanum compound are reacted alternately with ammonia gas at a surface to produce thin layers of lanthanum nitride on the surface. Particularly suitable lanthanum compounds are chosen from the class of lanthanum(III) amidinates. Replacing the ammonia in this process with water vapor can deposit lanthanum oxide.

In some embodiments, the reaction may be carried out in a manner to form films on substrates that may include holes or trenches. Coatings may also be placed on powders, wires or around and within complicated mechanical structures.

BRIEF DESCRIPTION OF THE DRAWINGS

The foregoing and various other aspects, features, and advantages of the present invention, as well as the invention itself, may be more fully appreciated with reference to the following detailed description of the invention when considered in connection with the following drawings. The drawings are presented for the purpose of illustration only and are not intended to be limiting of the invention, in which.

DETAILED DESCRIPTION OF THE INVENTION

Figure 1:
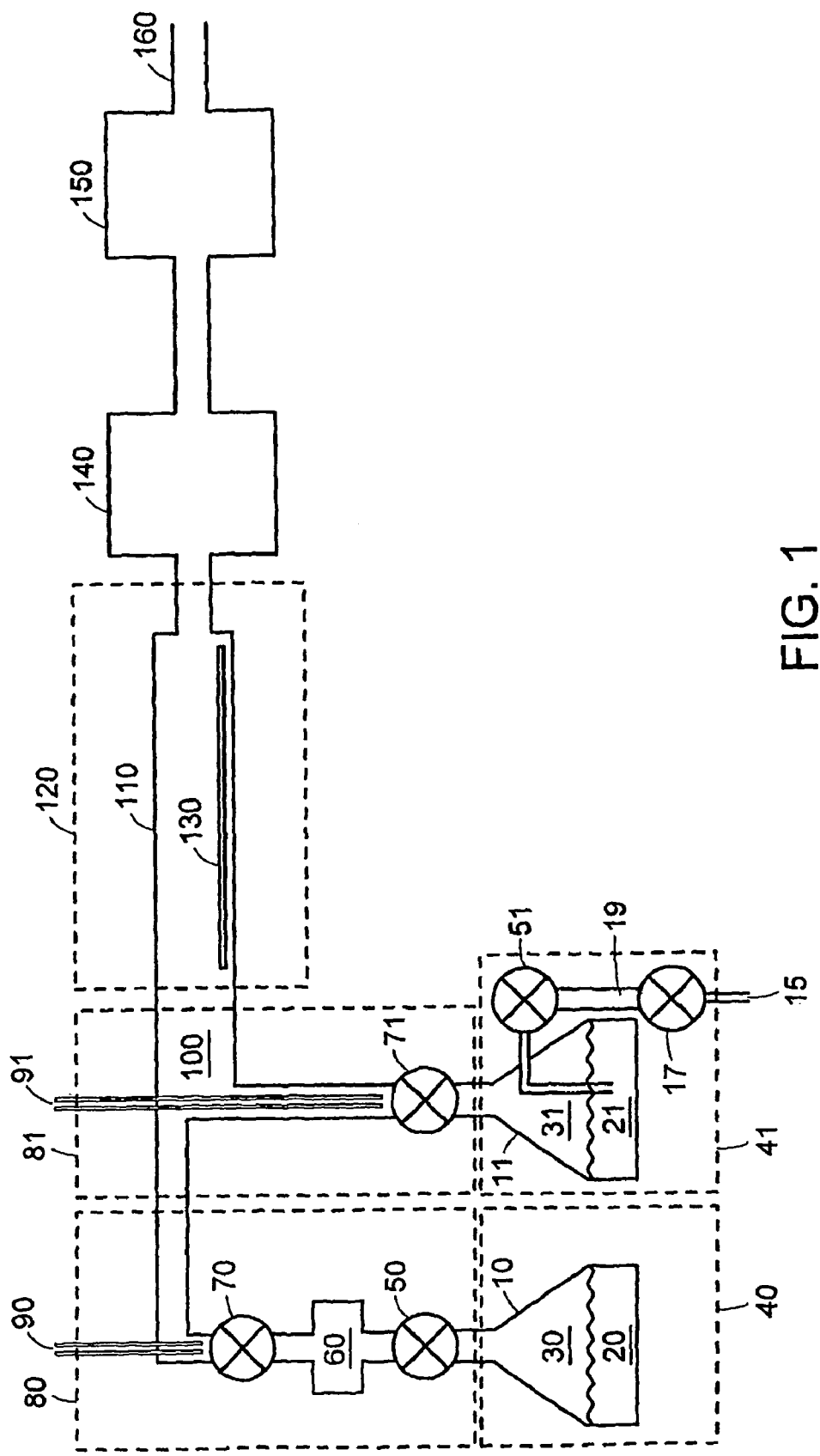
FIG. 1 is a cross-sectional illustration of an atomic deposition layer apparatus used in the practice of at least one embodiment of the invention.

The present invention provides a method for preparing a metal containing layer by atomic layer deposition from reactants including metal amidinates. In an atomic layer deposition process, doses of the metal compound vapor are supplied to a surface alternately with a vapor of a second reactant by an apparatus such as that shown in FIG. 1, which is described in detail later in this specification. Preferred metal amidinates include metal formamidinates and metal acetamidinates. Typical second reactants include hydrogen gas, ammonia gas or water vapor. When hydrogen gas is chosen as the second reactant, a metal may be deposited. When ammonia gas is chosen as the second reactant, a metal nitride is deposited. When water vapor is chosen as the second reactant, a metal oxide is deposited.

In one or more embodiments, precursors for monovalent metals include volatile metal(I) amidinates, $[M(I)(AMD)]_x$, where x=2, 3. Some of these compounds have a dimeric structure 1,

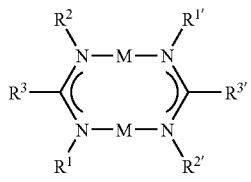

1 in which $R^1$, $R^2$, $R^3$, $R^{1'}$, $R^{2'}$ and $R^{3'}$ are groups made from one or more non-metal atoms. In some embodiments, $R^1$, $R^2$, $R^3$, $R^{1'}$, $R^{2'}$ and $R^{3'}$ may be chosen independently from hydrogen, alkyl, aryl, alkenyl, alkynyl, trialkylsilyl or fluoroalkyl groups or other non-metal atoms or groups. In some embodiments, $R^1$, $R^2$, $R^3$, $R^{1'}$, $R^{2'}$ and $R^{3'}$ are each independently alkyl or fluoroalkyl or silylalkyl groups containing 1 to 4 carbon atoms. Suitable monovalent metals include copper(I), silver (I), gold(I), and iridium(I). In one or more embodiments, the metal amidinate is a copper amidinate, and the copper amidinate comprises copper(I) N,N'-diisopropylacetamidinate, corresponding to taking $R^1$, $R^2$, $R^{1'}$ and $R^{2'}$ as isopropyl groups, and $R^3$ and $R^{3'}$ as methyl groups in the general formula 1. In one or more embodiments, the metal(I) amidinate is a trimer having the general formula $[M(I)(AMD)]_3$.

In one or more embodiments, divalent metal precursors include volatile metal(II) bis-amidinates, $[M(II)(AMD)_2]_x$, where x=1, 2. These compounds may have a monomeric structure 2,

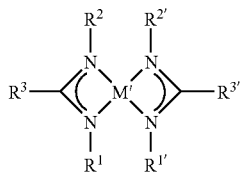

2 in which $R^1$, $R^2$, $R^3$, $R^{1'}$, $R^{2'}$ and $R^{3'}$ are groups made from one or more non-metal atoms. In one or more embodiments, dimers of this structure, e.g., $[M(n)(AMD)_2]_2$, may also be used. In some embodiments, $R^1$, $R^2$, $R^3$, $R^{1'}$, $R^{2'}$ and $R^{3'}$ may be chosen independently from hydrogen, alkyl, aryl, alkenyl, alkynyl, trialkylsilyl, or fluoroalkyl groups or other non-metal atoms or groups. In some embodiments, $R^1$, $R^2$, $R^3$, $R^{1'}$, $R^{2'}$ and $R^{3'}$ are each independently alkyl or fluoroalkyl or silylalkyl groups containing 1 to 4 carbon atoms. Suitable divalent metals include cobalt, iron, nickel, manganese, ruthenium, zinc, titanium, vanadium, chromium, europium, magnesium and calcium. In one or more embodiments, the metal(II) amidinate is a cobalt amidinate, and the cobalt amidinate comprises cobalt(II) bis N,N'-diisopropylacetamidinate), corresponding to taking $R^1$, $R^2$, $R^{1'}$ and $R^{2'}$ as isopropyl groups, and $R^3$ and $R^{3'}$ as methyl groups in the general formula 2.

In one or more embodiments, precursors for trivalent metals include volatile metal(III) tris-amidinates, $M(III)(AMD)_3$. Typically, these compounds have a monomeric structure 3,

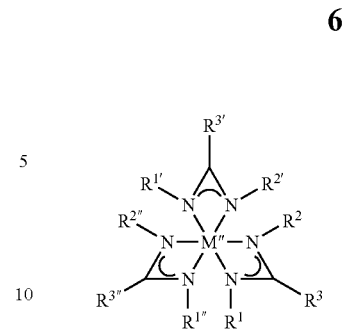

3 in which $R^1$, $R^2$, $R^3$, $R^{1'}$, $R^{2'}$, $R^{3'}$, $R^{1''}$ $R^{2''}$ and $R^{3''}$ are groups made from one or more non-metal atoms. In some embodiments, $R^1$, $R^2$, $R^3$, $R^{1'}$, $R^{2'}$, $R^{3'}$, $R^{1''}$, $R^{2''}$ and $R^{3''}$ may be chosen independently from hydrogen, alkyl, aryl, alkenyl, alkynyl, trialkylsilyl, halogen or partly fluorinated alkyl groups. In some embodiments, $R^1$, $R^2$, $R^3$, $R^{1'}$, $R^{2'}$, $R^{3'}$, $R^{1''}$, $R^{2''}$ and $R^{3''}$ are each independently alkyl groups containing 1 to 4 carbon atoms. Suitable trivalent metals include lanthanum, praseodymium and the other lanthanide metals, yttrium, scandium, titanium, vanadium, niobium, tantalum, chromium, iron, ruthenium, cobalt, rhodium, iridium, aluminum, gallium, indium, and bismuth. In one or more embodiments, the metal(III) amidinate is a lanthanum amidinate, and the lanthanum amidinate comprises lanthanum(III) tris(N,N'-di-tert-butylacetamidinate), corresponding to taking $R^1$, $R^2$, $R^{1'}$, $R^{2'}$, $R^{1''}$ and $R^{2''}$ as tent-butyl groups and $R^3$, $R^{3'}$, and $R^{3''}$ as methyl groups in the general formula 3.

As used herein, metal amidinates having the same ratio of metal to amidinate as the monomer, but varying in the total number of metal/amidinate units in the compound are referred to as "oligomers" of the monomer compound. Thus, oligomers of the monomer compound $M(II)AMD_2$ include $[M(II)(AMD)_2]_x$, where x is 2, 3, etc. Similarly, oligomers of the monomer compound M(I)AMD include $[M(I)AMD]_x$, where x is 2, 3, etc.

Metal amidinates may be prepared using any suitable method. One method to make a metal amidinate precursor involves first forming a lithium amidinate by reaction of a 1,3-dialkylcarbodiimide with an alkyllithium compound:

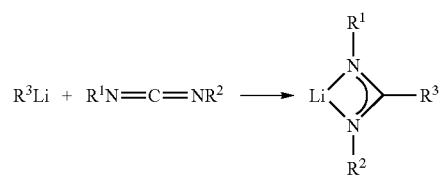

Then the lithium amidinate is reacted with a metal halide to form a metal amidinate:

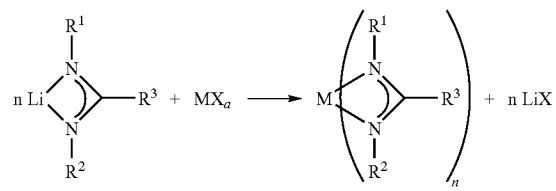

Unsymmetrical carbodiimides (in which $R^1$ is not the same as $R^2$), as well as symmetric carbodiimides ($R^1=R^2$), can be synthesized by the following sequence of reactions:

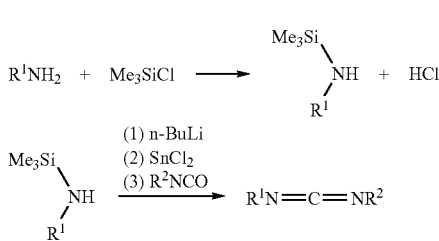

A wide variety of alkylamines and alkylisocyanates are commercially available to supply the $R^1$ and $R^2$ alkyl groups. Different $R^3$ alkyl groups can be supplied by the use of appropriate alkyllithium compounds.

Another method for making metal amidinates uses N,N'-dialkylamidines,

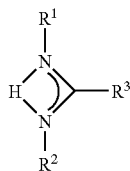

rather than carbodiimides.

An amidine may be converted into a metal amidinate by reacting the amidine with a metal hydride (R=H), a metal alkyl (R=alkyl) or a metal alkylamide (R=dialkylamide):

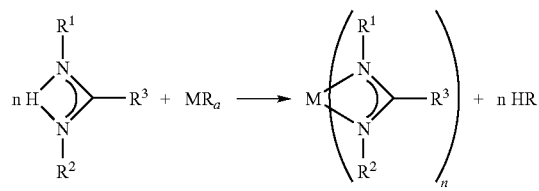

Alternatively, this last reaction may be used to form an alkali metal salt of the amidine, which is then subsequently reacted with a metal halide to form the desired metal amidine.

N,N'-dialkylamidines may be synthesized by any convenient method known in the art of organic chemistry. Symmetric amidines ($R^1=R^2$) may be formed by condensation of amines with nitriles catalyzed by lanthanum trifluoromethanesulfonate (also known as lanthanum triflate):

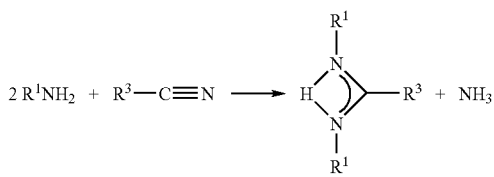

Unsymmetric amidines (R1 not equal to R2), as well as symmetric amidines, may be synthesized by the following reactions starting from an amide. Some amides are commercially available, and others may be synthesized by reaction of an organic acid chloride with an amine:

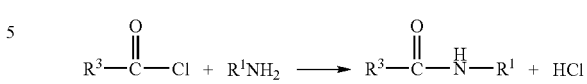

Next, the amide is reacted with trifluoromethanesulfonic anhydride (also known as triflic anhydride) in the presence of an organic base such as pyridine, to form an iminium salt:

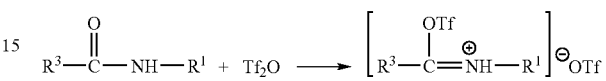

This intermediate iminium salt is then reacted with an alkylammonium chloride $R^2NH_3Cl$ and then with a base such as NaOH to form the desired free amidine:

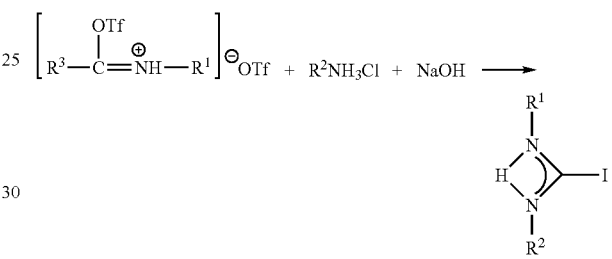

$R^2$ In order to make these reactions as facile as possible, the group $R^2$ is chosen to be more sterically hindered than the $R^1$ group, for the synthesis of unsymmetric amidines.

Liquid precursors generally have several advantages in practicing the invention. If the melting point of the metal amidinate is below room temperature, then the liquid compound can be made in high purity by fractional distillation. In contrast, solid materials are more difficult to purify by sublimation, which is less effective than distillation in removing impurities. Air-sensitive liquid compounds are also generally easier to handle and transfer than are solids.

Metal amidinates with lower melting points can be made by using longer chain alkyl groups for $R^1$, $R^2$ and/or $R^3$. Unsymmetrical metal amidinates (in which $R^1$ is not the same as $R^2$) generally have lower melting points than symmetric metal amidinates. Alkyl groups with more than one stereoisomer, such as sec-butyl, also lead to lower melting points. Use of one or more of these strategies can lead to desirable liquid precursors, rather than less desirable solid compounds.

Low melting points are also desirable in supplying vapor for a deposition process according to this invention. If the melting point of a compound is lower than the temperature at which the compound is vaporized, then the liquid source of vapor generally has faster kinetics of vaporization than solid compounds have. Also, sublimation of a solid often leaves its surface covered with a residue of less volatile material that impedes further vaporization. In a liquid source, on the other hand, any non-volatile residue may precipitate into the bulk of the liquid, leaving the liquid surface clean and capable of desirable rapid evaporation.

According to one or more embodiments of the present invention, a metal amidinate is introduced onto a substrate as a vapor. Vapors of precursors may be formed by conventional methods from either liquid or solid precursors. In one or more embodiments, a liquid precursor may be vaporized by nebulization into a carrier gas preheated above the vaporization temperature, e.g., to about 100 to 200° C. The nebulization may be carried out pneumatically, ultrasonically, or by other suitable methods. Solid precursors to be nebulized may be dissolved in organic solvents, including hydrocarbons such as decane, dodecane, tetradecane, toluene, xylene and mesitylene, ethers, esters, ketones and chlorinated hydrocarbons. Solutions of liquid precursors generally have lower viscosities than pure liquids, so that in some cases it may be preferable to nebulize and evaporate solutions rather than pure liquids. The precursor liquid or precursor solutions may also be evaporated with thin-film evaporators, by direct injection of the liquids or solutions into a heated zone, or by heating in a bubbler. Commercial equipment for vaporization of liquids is made by MKS Instruments (Andover, Mass.), ATMI, Inc. (Danbury, Conn.), Novellus Systems, Inc. (San Jose, Calif.) and COVA Technologies (Colorado Springs, Colo.). Ultrasonic nebulizers are made by Sonotek Corporation (Milton, N.Y.) and Cetac Technologies (Omaha, Nebr.).

The metal precursors of the present invention may be reacted with a reducing agent, e.g., hydrogen gas, to form films of the metal. For example, copper(I) N,N'-diisopropylacetamidinate may be reacted with hydrogen gas to form copper metal. In other embodiments, the metal precursors of the present invention may also be reacted with other suitably reactive reducing compounds to form metals. In some embodiments, the metal precursors of the present invention may be reacted with ammonia gas to form metal nitrides. For example, cobalt(II) bis(N,N'-diisopropylacetamidinate) may be reacted with ammonia gas to form cobalt nitride. In other embodiments, the metal precursors of the present invention may be reacted with water vapor to form metal oxides. For example, lanthanum(III) tris(N,N-di-tert-butylacetamidinate) may be reacted with water vapor to form lanthanum oxide.

The process of the invention may be carried out using atomic layer deposition (ALD). ALD introduces a metered amount of a first reactant into a deposition chamber having a substrate therein for layer deposition. A thin layer of the first reactant is deposited on the substrate. Then any unreacted first reactant and volatile reaction by-products are removed by a vacuum pump and, optionally, a flow of inert carrier gas. A metered amount of a second reactant component is then introduced into the deposition chamber. The second reactant deposits on and reacts with the already deposited layer from the first reactant. Alternating doses of first and second reactants are introduced into the deposition chamber and deposited on the substrate to form a layer of controlled composition and thickness. The time between doses may be on the order of seconds and is selected to provide adequate time for the just-introduced component to react with the surface of the film and for any excess vapor and byproducts to be removed from the headspace above the substrate. It has been determined that the surface reactions are self-limiting so that a reproducible layer of predictable composition is deposited. As will be appreciated by one of ordinary skill in the art, deposition processes utilizing more than two reactant components are within the scope of the invention.

In one or more embodiments of me invention, a 6-port sampling valve (Valco model EP4C6WEPH, Valco Instruments, Houston, Tex.) normally used for injecting samples into gas chromatographs may be used to deliver pulses of reactant gas. Each time that the valve is turned by computer control, a measured volume of gas in the "sample loop" flows into the deposition chamber. A constant flow of carrier gas helps to clear residual reactant gas from the tube leading into the heated deposition zone. This delivery method is convenient for reactant gases such as hydrogen and ammonia.

Doses of reactants whose vapor pressures are higher than the pressure in the deposition chamber can be introduced using apparatus such as that illustrated in FIG. 1. For example, water has a vapor pressure (about 24 Torr at room temperature) that is much higher than a typical pressure in the deposition chamber (usually less than 1 Torr). Such a volatile precursor 20 has vapor 30 that is introduced into the heated deposition chamber 110 by the use of a pair of air-actuated diaphragm valves, 50 and 70 (Titan II model made by Parker-Hannifin, Richmond Calif.). The valves are connected by a chamber 60 having a measured volume V, and this assembly is placed inside an oven 80 held at a controlled temperature $T_2$. The pressure of the reactant vapor 30 in the precursor reservoir 10 is equal to the equilibrium vapor pressure $P_{eq}$ of the solid or liquid reactant 20 at a temperature $T_1$ determined by the surrounding oven 40. The temperature $T_1$ is chosen to be high enough so that the precursor pressure $P_{eq}$ is higher than the pressure $P_{dep}$ in the deposition chamber. The temperature $T_2$ is chosen to be higher than $T_1$ so that only vapor and no condensed phase is present in the valves 50 and 70 or the chamber 60. In the case of a gaseous reactant, this delivery method can also be used. The gas pressure in volume V can be set in this case by a pressure regulator (not shown) that reduces its pressure from the pressure in the vessel storing the gaseous reactant.

Carrier gas (such as nitrogen gas) flows at a controlled rate into inlet 90 in order to speed the flow of the reactants into the deposition chamber and the purging of reaction byproducts and un-reacted reactant vapor. A static mixer may be placed in the tubing 100 leading into the reactor, to provide a more uniform concentration of the precursor vapor in the carrier gas as it enters the deposition chamber 110 heated by furnace 120 and containing one or more substrates 130. The reaction byproducts and un-reacted reactant vapors are removed by trap 140 before passing into a vacuum pump 150. Carrier gas exits from exhaust 160.

In operation, valve 70 is opened so that the pressure inside chamber 60 is reduced to a value $P_{dep}$ close to that of the deposition chamber 110. Then valve 70 is closed and valve 50 is opened to admit precursor vapor from precursor reservoir 10 into chamber 60. Then valve 50 is closed so that the volume V of chamber 60 contains vapor of the precursor at a pressure $P_{eq}$. Finally, valve 70 is opened to admit most of the precursor vapor contained in chamber 60 into the deposition chamber. The number of moles, n, of precursor delivered by this cycle can be estimated by assuming that the vapor obeys the ideal gas law:

$$n = (P_{eq} - P_{dep})(V/RT_1)$$

where R is the gas constant. This expression also assumes that carrier gas from tube 90 does not enter chamber 60 through valve 70 during the brief time that it is open to release the precursor vapor. If mixing of carrier gas with the precursor vapor does occur during the time that valve 70 is open, then a larger dose of precursor vapor may be delivered, up to a maximum value $$n = (P_{eq})(V/RT_1)$$

if all the residual precursor vapor in chamber 60 is displaced by carrier gas. For precursors with relatively high vapor pressure ($P_{eq} \gg P_{dep}$), there is usually not much difference between these two estimates of the precursor dose.

This cycle of delivering precursor 20 is repeated if necessary until the required dose of precursor 20 has been delivered into the reaction chamber. Typically, in an ALD process, the dose of precursor 20 delivered by this cycle (or several such cycles repeated to give a larger dose) is chosen to be large enough to cause the surface reactions to go to completion (also called "saturation").

In the case of precursors with vapor pressure so low that $P_{eq}$ is less than $P_{dep}$ the methods described above will not deliver any precursor vapor into the deposition chamber. The vapor pressure can be increased by raising the temperature of the reservoir, but in some cases a higher temperature would result in thermal decomposition of the precursor. Metal amidinate precursors often have vapor pressures that are less than the operating pressure in the deposition chamber. In the case of a thermally sensitive precursor 21 with low vapor pressure, its vapor 31 may be delivered using the apparatus in FIG. 1. The chamber 19 is first pressurized with carrier gas delivered through tube 15 and valve 17 from a pressure controller (not shown). Valve 17 is then closed and valve 51 opened to allow the carrier gas to pressurize precursor reservoir 11 to pressure $P_{tot}$. The mole fraction of precursor vapor in the vapor space 31 of reservoir 11 is then $P_{eq}/P_{tot}$. Valve 51 is closed and then valve 71 opened to deliver the dose of reactant vapor 31. If $P_{tot}$ is set to a pressure larger than the pressure $P_{dep}$ in the deposition chamber, then the number of moles delivered in a dose can be estimated from the equation $$n=(P_{eq}/P_{tot})(P_{tot}-P_{dep})(V/RT_1),$$

where V is the volume of the vapor space 31 in chamber 11 and $T_1'$ is the temperature maintained by oven 41. Oven 81 is maintained at a temperature $T_2''$ that is high enough above $T_1'$ to avoid condensation. If carrier gas from tube 91 enters the volume 31 during the time that the valve 71 is open, then a dose somewhat larger than this estimate may be delivered. By making the volume V large enough, a precursor dose that is certainly large enough to saturate the surface reaction may be delivered. If the vapor pressure $P_{eq}$ is so low that the required volume V would be impracticably large, then additional doses from volume V may be delivered before delivering a dose of the other reactant.

In one or more embodiments, the apparatus of FIG. 1 may include two delivery chambers that are alike, e.g., both are used to deliver samples having vapor pressures higher than or lower than the deposition pressure.

In an isothermal deposition zone 110, material is generally deposited on all surfaces exposed to the precursor vapors, including substrates and the interior chamber walls. Thus it is appropriate to report the precursor doses used in terms of moles divided by the total area of the substrates and exposed chamber walls. In some cases, deposition also occurs on part or all of the back side of the substrates, in which case that area should also be included in the total area.

The invention may be understood with reference to the following examples which are for the purpose of illustration only and which are not limiting of the invention, the full scope of which is set forth in the claims that follow.

All reactions and manipulations described in these examples were conducted under a pure nitrogen atmosphere using either an inert atmosphere box or standard Schlenk techniques. Tetrahydrofuran (THF), ether, hexanes and acetonitrile were dried using an Innovative Technology solvent purification system and stored over 4 A molecular sieves. Sec-butylamine was dried by distillation from barium oxide. Methyllithium, tert-butyllithium, 1,3-diisopropylcarbodiimide, 1,3-di-tert-butylcarbodiimide, CuBr, AgCl, CoCl$_2$, NiCl$_2$, MnCl$_2$, MgCl$_2$, SrCl$_2$, TiCl$_3$, VCl$_3$, BiCl$_3$, RUCl$_3$, Me$_3$Al (trimethylaluminum), (CF$_3$SO$_3$)$_3$La (La triflate), La and Pr were used as received from Aldrich Chemical Company. The metal compounds produced by these procedures generally react with moisture and/or oxygen in the ambient air, and should be stored and handled under an inert, dry atmosphere such as pure nitrogen or argon gas.

Example 1

Synthesis of (N,N'-diisopropylacetamidinato)copper ([Cu($^i$Pr-AMD)]$_2$)

A solution of methyllithium (1.6 M in ether, 34 mL, 0.054 mol) in ether was added dropwise to a solution of 1,3-diisopropylcarbodiimide (6.9 g, 0.055 mol) in 100 mL of ether at −30° C. The mixture was warmed up to room temperature and stirred for 4 h. The resultant colorless solution was then added to a solution of copper bromide (7.8 g, 0.054 mol) in 50 mL of ether. The reaction mixture was stirred for 12 h under the exclusion of light. All volatiles were then removed under reduced pressure, and the resulting solid was extracted with hexanes (100 mL). The hexanes extract was filtered through a pad of Celite on a glass frit to afford a pale yellow solution. Concentration of the filtrate and cooling it to −30° C. afforded 9.5 g of colorless crystals as a product (83%). Sublimation: 70° C. at 50 mTorr. $^1$H NMR (C$_6$D$_6$, 25° C.): 1.16 (d, 12H), 1.65 (s, 3H), 3.40 (m, 2H). Anal. Calcd for C$_{16}$H$_{34}$N$_4$Cu$_2$: C, 46.92; H, 8.37; N, 13.68. Found: C, 46.95; H, 8.20; N, 13.78.

Figure 2:
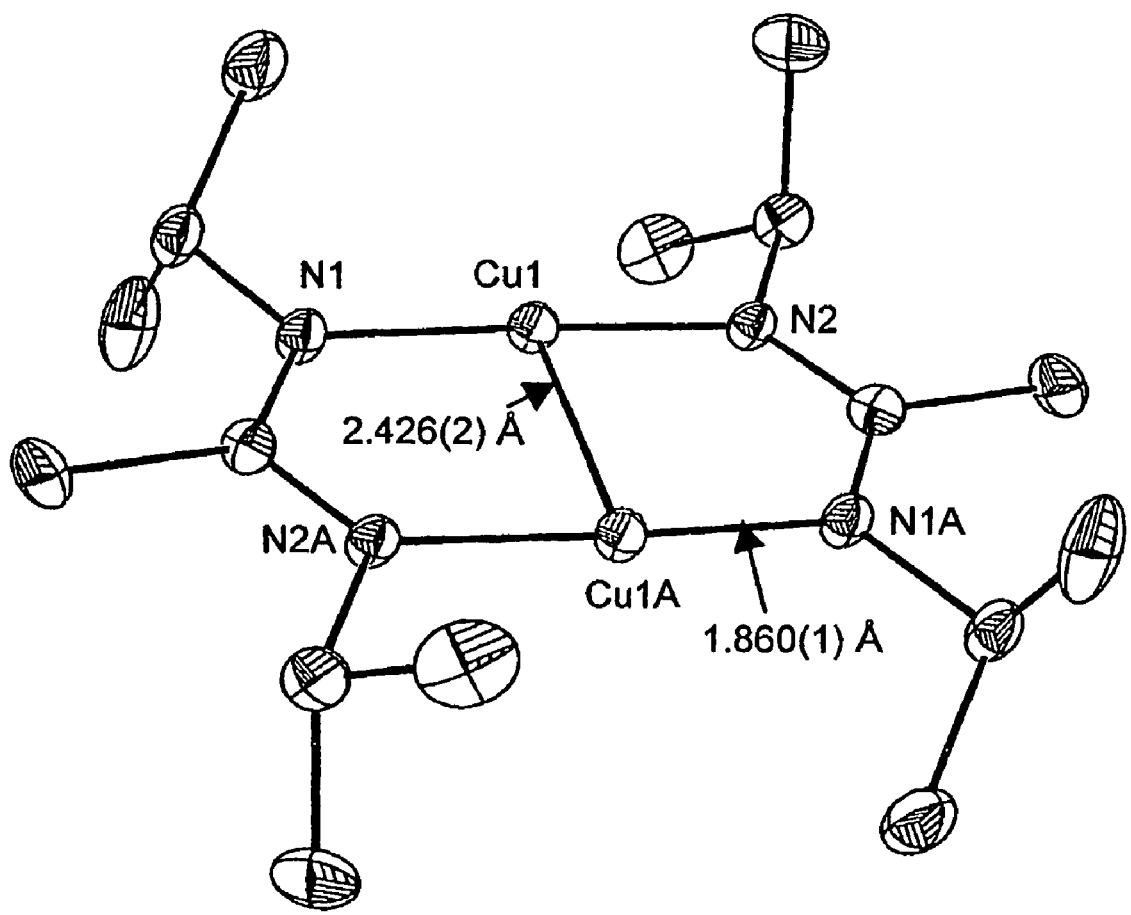
FIG. 2 is the molecular structure of a copper precursor used in the practice of at least one embodiment of the invention.

A [Cu($^i$Pr-AMD)]$_2$ crystal was structurally characterized by X-ray crystallography. [Cu($^i$Pr-AMD)]$_2$, shown in FIG. 2, is a dimer in the solid state in which amidinate ligands bridge copper metal atoms in a $\mu\eta^1\eta^1$-fashion. The average Cu—N distance is 1.860(1) Å. The geometries of the five-membered rings of Cu—N—C—N—Cu are planar with centrosymmetry imposed by the crystal structure.

Example 2

Synthesis of bis(N,N$^i$-diisopropylacetamidinato) cobalt ([Co($^i$Pr-AMD)$_2$])

This compound was obtained in a similar manner as described for [Cu($^i$Pr-AMD)], but with a 1:1 mixture of ether and THF as solvent. Recrystallization in hexanes at −30° C. gave dark green crystals as product (77%). Sublimation: 40° C. at 50 mTorr. m.p.: 72° C. Anal. Calcd for C$_{16}$H$_{34}$N$_4$Co: C, 56.29; H, 10.04; N, 16.41. Found: C, 54.31; H, 9.69; N, 15.95.

Figure 3:
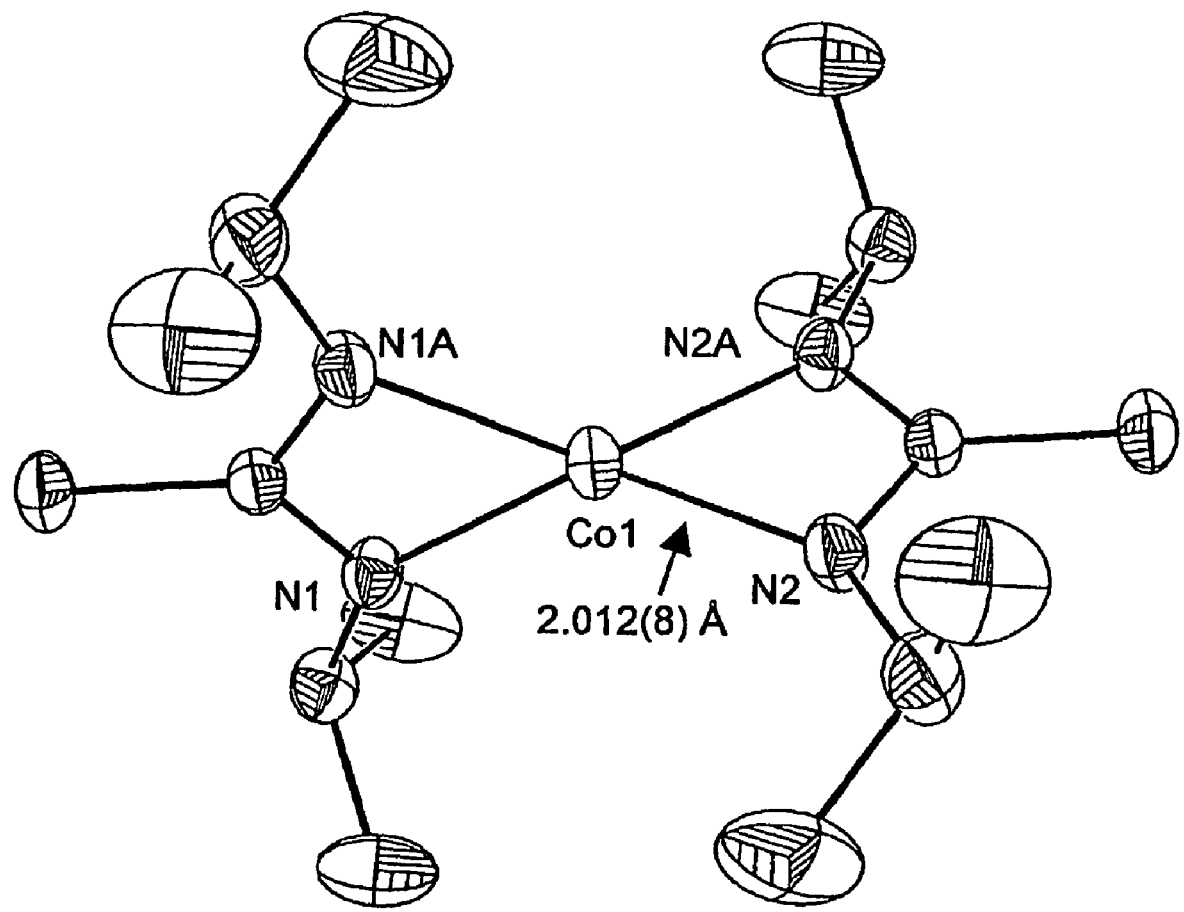
FIG. 3 is the molecular structure of a cobalt precursor used in the practice of at least one embodiment of the invention.

Co($^i$Pr-AMD)$_2$, shown in FIG. 3, is monomeric with two amidinate ligands arranged about each cobalt atom in a distorted tetrahedral environment The average Co—N distance is 2.012(8) Å. The Co—N—C—N four-membered rings are planar with an imposed mirror plane.

Example 3

Synthesis of Cobalt bis(N,N$^i$di-tert-butylacetamidinate) ([Co($^t$Bu-AMD)$_2$])

This compound was obtained in a manner similar to ([Co($^i$Pr-AMD)$_2$]) in Example 2, using 1,3-di-tert-butylcarbodiimide in place of 1,3-diisopropylcarbodiimide. Dark blue crystals (84%). Sublimation: 45° C. at 50 mtorr. m.p.: 90° C.

Anal. Calcd for $C_{20}H_{42}N_4Co$: C, 60.43; H, 10.65; N, 14.09. Found: C, 58.86; H, 10.33; N, 14.28.

Example 4

Synthesis of Lanthanum tris(N,N'-diisopropylacetamidinate)([La($^i$Pr-AMD)$_3$])

Following a similar procedure as described above for [Co ($^i$Pr-AMD)$_2$], but using LaCl$_3$(THF)$_2$ in place of CoCl$_2$, off-white solids were obtained as a product by sublimation of the crude solid material. Sublimation: 80° C. at 40 mtorr. $^1$H NMR ($C_6D_6$ 25° C.): 1.20 (d, 36H), 1.67 (s, 18H), 3.46 (m, 6H). Anal. Calcd for $C_{24}H_{51}N_6La$: C, 51.24; H, 9.14; N, 14.94. Found: C, 51.23; H, 8.22; N, 14.57.

Example 5

Synthesis of lanthanum tris(N,N'-diisopropyl-2-tert-butylamidinate) ([La($^i$Pr-$^t$BuAMD)$_3$]·1/2 $C_6H_{12}$)

Following a similar procedure as described above for [Co ($^i$Pr-AMD)$_2$], but using LaCl$_3$(THF)$_2$, off-white solids were obtained as a product by sublimation of the crude solid materials. Colorless crystals (80%). Sublimation: 120° C. at 50 mtorr. m.p.: 140° C. $^1$H NMR ($C_6D_6$, 25° C.): 1.33 (br, 21H), 4.26 (m, 6H). Anal. Calcd for $C_{33}H_{75}N_6La$: C, 57.04; H, 10.88; N, 12.09. Found: C, 58.50; H, 10.19; N, 11.89.

Example 6

Synthesis of bis(N,N'-diisopropylacetamidinato)iron ([Fe($^i$Pr-AMD)$_2$]$_2$)

Following a similar procedure as described above for [Co ($^i$Pr-AMD)$_2$]$_2$, but using FeCl$_2$, yellow-green solids [Fe($^i$Pr-AMD)$_2$]$_2$ were obtained as a product upon evaporation of the solvent from the hexanes extract. Sublimation: 70° C. at 50 mtorr. m.p.: 110° C.

Example 7

Synthesis of iron bis(N,N'-di-tert-butylacetamidinate) ([Fe($^t$Bu-AMD)$_2$])

Following a similar procedure as described above for [Fe ($^i$Pr-AMD)$_2$]$_2$, but using 1,3-di-tert-butylcarbodiimide in place of 1,3-diisopropylcarbodiimide, white crystals (77%) were obtained. Sublimation: 55° C. at 60 mtorr. m.p.: 107° C. Anal. Calcd for $C_{20}H_{42}N_4Fe$: C, 60.90; H, 10.73; N, 14.20. Found: C, 59.55; H, 10.77; N, 13.86.

Example 8

Synthesis of bis(N,N'-diisopropylacetamidinato) nickel ([Ni($^i$Pr-AMD)$_2$])

Following a similar procedure as described in Example 2 for [Co($^i$Pr-AMD)$_2$], but using NiCl$_2$, and refluxing the reaction mixture overnight, brown solids [Ni($^i$Pr-AMD)$_2$] were obtained as a product upon evaporation of the solvent from the hexanes extract. Brown crystals (70%). Sublimation: 35° C. at 70 mtorr. m.p.: 55° C. Anal. Calcd for $C_{16}H_34N_4Ni$: C, 56.34; H, 10.05; N, 16.42. Found: C, 55.22; H, 10.19; N, 16.12.

Example 9

Synthesis of bis(N,N'-diisopropylacetamidinato) manganese ([Mn($^i$Pr-AMD)$_2$]$_2$)

Following a similar procedure as described above for [Co ($^i$Pr-AMD)$_2$], but using MnCl$_2$) solid [Mn($^i$Pr-AMD)$_2$]$_2$ was obtained as a product upon evaporation of the solvent from the hexanes extract. Yellowish green crystals (79%). Sublimation: 65° C. at 50 mtorr. Anal. Calcd for $C_{32}H_{68}N_8Mn_2$: C.56.96; H, 10.16; N, 16.61. Found: C, 57.33; H, 9.58; N, 16.19.

Example 10

Synthesis of Manganese bis^A^'-di-tert-butylacetamidinate) ([Mn($^t$Bu-AMD)$_2$])

Following a similar procedure as described above for [Mn ($^i$Pr-AMD)$_2$], but using 1,3-di-tert-butylcarbodiimide in place of 1,3-diisopropylcarbodiimide, pale yellow crystals (87%) were obtained. Sublimation: 55° C. at 60 mtorr. m.p.: 100° C.

Example 11

Synthesis of tris(N,N'-diisopropylacetamidinato) titanium [Ti($^i$Pr-AMD)$_3$])

Following a similar procedure as described above for [La $^i$Pr-AMD)$_3$], but using TiCl$_3$ in place of LaCl$_3$(THF)$_2$, [Ti($^i$Pr-AMD)$_3$] was obtained as a product upon evaporation of the solvent from the hexanes extract. Brown crystals (70%). Sublimation: 70° C. at 50 mtorr. Anal. Calcd for $C_{24}H_{51}N_6Ti$: C, 61.13; H, 10.90; N, 17.82. Found: C, 60.22; H, 10.35; N, 17.14.

Example 12

Synthesis of tris(N,N'-diisopropylacetamidinato) vanadium ([V($^i$Pr-AMD)$_3$])

Following a similar procedure as described above for [Ti ($^i$Pr-AMD)$_3$], but using VCl$_3$ in place of TiCl$_3$, [V($^i$Pr-AMD)$_3$] was obtained as a product upon evaporation of the solvent from the hexanes extract. Red-brown powder (80%). Sublimation: 70° C. at 45 mtorr.

Example 13

Synthesis of Silver (N,N'-di-isopropylacetamidinate) ([Ag($^i$Pr-AMD)]$_x$ (x=2 and x=3)

These two compounds were prepared simultaneously in the same manner as described for [Cu($^i$Pr-AMD)], and obtained as a 1:1 mixture of dimer and trimer. Colorless crystals (90%). Sublimation: 80° C. at 40 mtorr. m.p.: 95° C. $^1$H NMR ($C_6D_6$ 25° C.): 1.10 (d, dimer), 1.21 (d, trimer), 1.74 (s, trimer), 1.76 (s, dimer), 3.52 (m, peaks for dimer and trimer are not well resolved.) Anal. Calcd for [$C_8H_{17}N_2Ag$]$_x$: C, 38.57; H, 6.88; N, 11.25. Found: C, 38.62; H, 6.76; N, 11.34.

Example 14

Atomic Layer Deposition of Copper Metal

The apparatus of FIG. 1 was used to deposit copper metal. Copper(I) N,N'-diisopropylacetamidinate dimer was placed in a stainless steel container 11 with vapor volume 125 cubic centimeters and heated to 85° C., at which temperature it has a vapor pressure of about 0.15 Torr. Doses of 1.0 micromoles of the copper precursor were introduced by pressurizing the chamber to 10 Ton with nitrogen carrier gas. Hydrogen was introduced in doses of 1.4 millimole using a gas-chromatography sampling valve. The area of the substrates 130 and the heated walls of chamber 110 add up to about $10^3$ square centimeters. Thus, a dose of copper precursor was $1\times10^9$ moles/cm$^2$ and a dose of hydrogen was $1.4\times10^{-6}$ moles/cm$^2$. The "exposure" is defined as the product of the partial pressure of a precursor vapor in the deposition zone and the time that this vapor is in contact with a given point on the surface of the substrate. The exposure of the substrate to the copper precursor was $2.3\times10^4$ Langmuirs/cycle and its exposure to hydrogen was $3.4\times10^7$ Langmuirs/cycle.

One silicon substrate 130 was prepared by dissolving its native oxide by placing it in dilute hydrofluoric acid solution for a few seconds. Next the substrate was irradiated by ultraviolet light (e.g. UV mercury lamp) in air until the surface became hydrophilic (about two minutes). Then a substrate 130 was placed in chamber 110 and heated to a temperature of 225° C. Another silicon substrate with narrow holes (4.5:1 ratio of length to diameter) was treated similarly and placed in chamber 110. Substrates of glassy carbon were cleaned with 10% aq. HF (5s), deionized water (30s), and isopropanol (10s) prior to drying and UV cleaning Substrates of glass and sputtered platinum and copper on silicon were cleaned with isopropanol (10s) and dried.

Carrier gas flowed for 10 seconds between the alternating doses of copper precursor and hydrogen. 500 cycles were completed, and then the heater for the deposition chamber was turned off. After the substrates cooled to room temperature, they were removed from the reactor. The carbon and silicon substrates were examined by Rutherford Backscattering Spectroscopy and found to have a film of pure copper, $8\times10^{16}$ atoms/cm$^2$ thick or $1.4\times10^{-7}$ moles/cm$^2$ thick.

Figure 4:
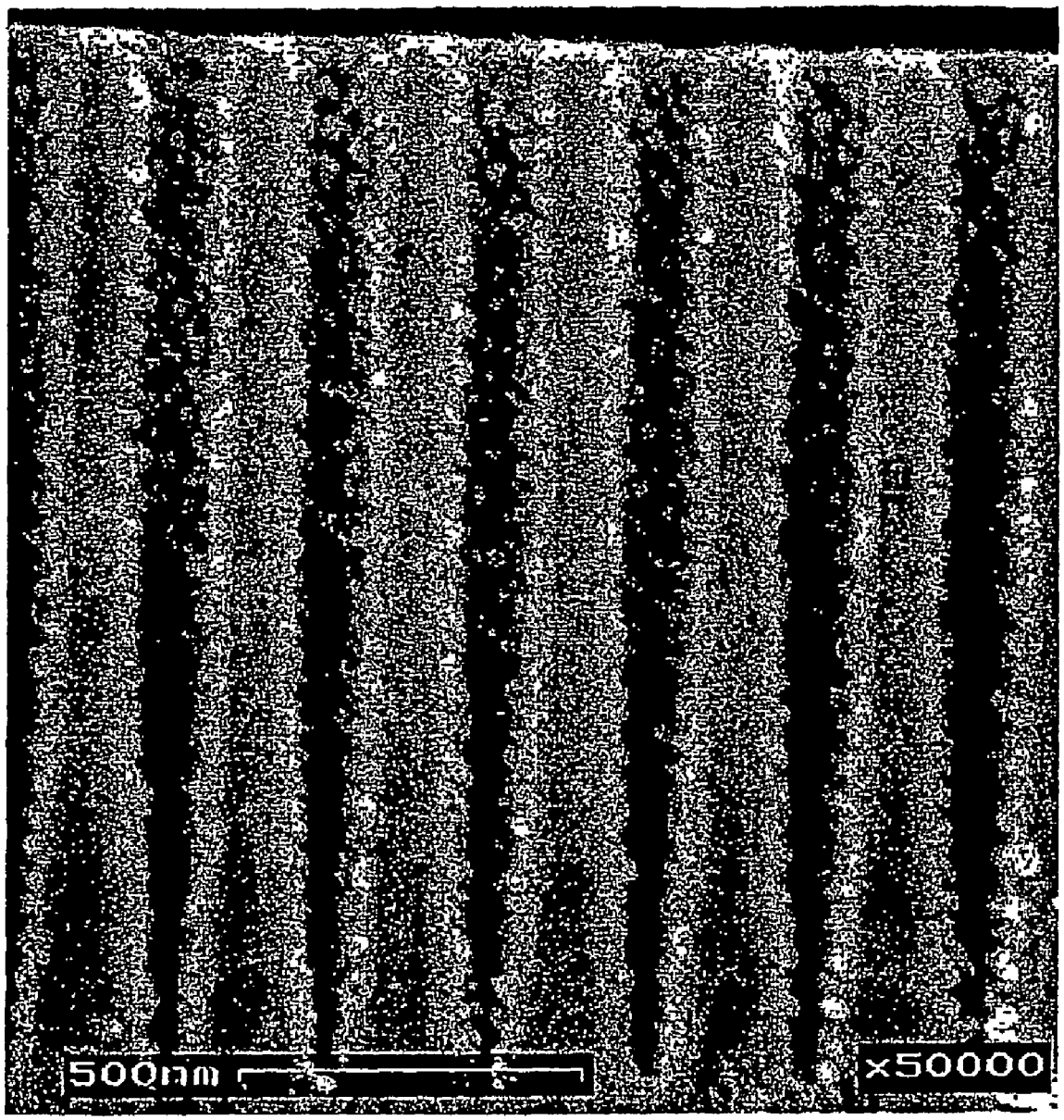
FIG. 4 is a cross-sectional scanning electron micrograph of narrow holes whose walls are coated with copper metal using one embodiment of the invention.

The silicon wafer with the holes was cleaved and a scanning electron micrograph (SEM) was taken of a cross section of the holes. The micrograph in FIG. 4 shows that copper coats the entire inside surface of the holes with aspect ratio (defined as the ratio of length to diameter) of about 10:1; thus this process for ALD of copper demonstrates excellent step coverage.

Example 15

Demonstration that the Surface Reactions are Self-Limited

Example 14 was repeated, except that the doses of both reactants were doubled. The film thickness and its properties were unchanged from those of Example 1. This result shows that the surface reactions are self-limiting.

Example 16

Demonstration that the Film Thickness Varies Linearly with the Number of Cycles Example 14 was repeated, except that 1000 cycles were used instead of 500 cycles. Twice as much material was deposited. This result shows that each self-limiting reaction reproduces the conditions needed for the other reaction to begin again, and that there are no significant delays in initiating reactions or nucleating growth on the surface of the substrate.

Example 17

Figure 6:
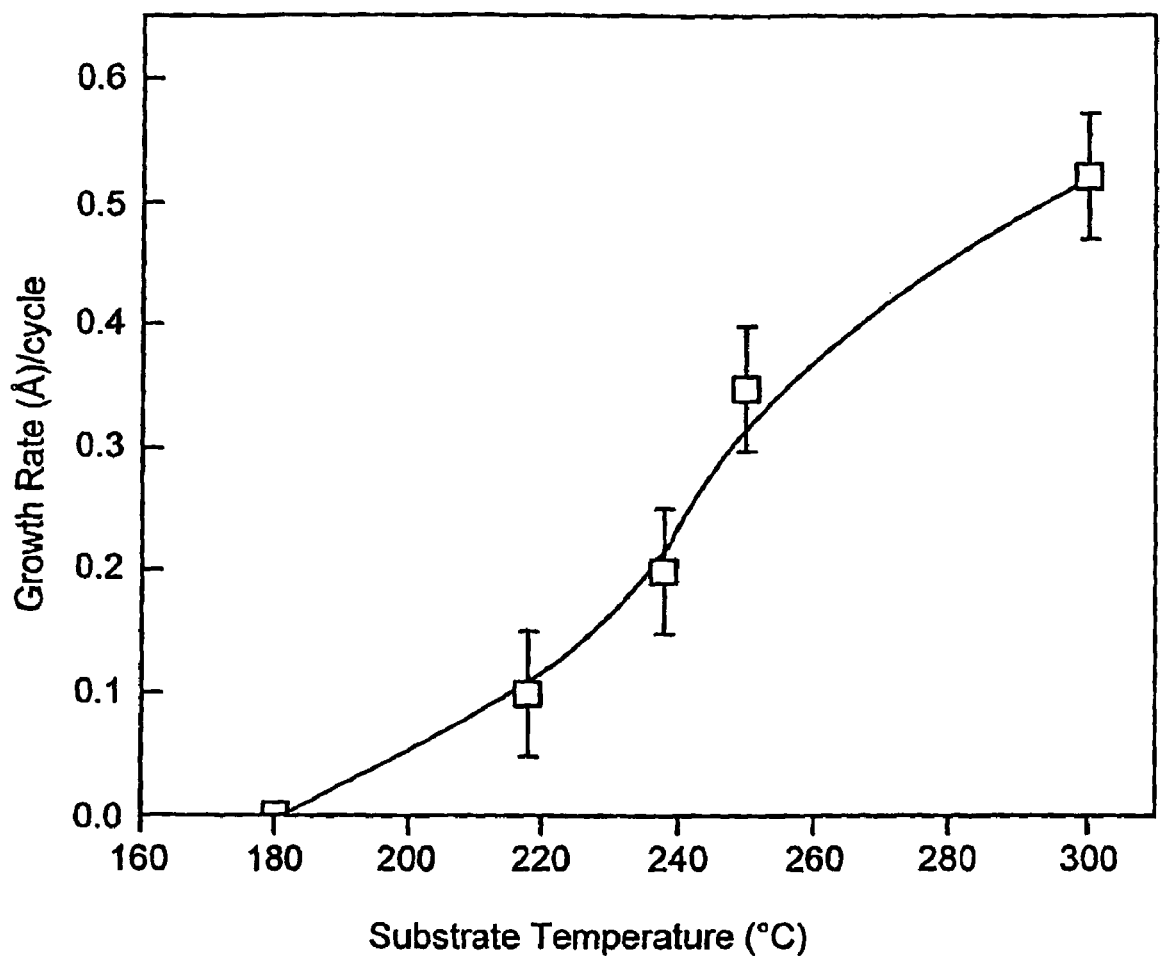
FIG. 6 is a plot of the thickness of copper deposited in each ALD cycle, as a function of substrate temperature.

Demonstration of a Range of Temperatures for Atomic Layer Deposition of Copper Example 14 was repeated, except that the substrate temperatures were varied within the range from 180° C. to 300° C. Similar results were obtained, except that the thickness per cycle varied with temperature as shown in FIG. 6. At substrate temperatures below 180° C., no deposition of copper was observed. This observation shows that walls of a reaction chamber remain free of unwanted copper deposits if the wall temperature is kept below 180° C. and above the dew point of the precursor.

Example 18

Atomic Layer Deposition of Cobalt Metal

Example 14 was repeated, except that cobalt bis(N,N'-diisopropylacetamidinate) kept at 75° C. was used in place of the copper precursor and the substrate temperature was raised to 300° C. A silicon substrate previously coated with silicon dioxide and then with tungsten nitride was placed in the deposition chamber, along with a fused silica capillary tube having inner diameter 20 micrometers. In each cycle, the dose of cobalt precursor was $4\times10^{-9}$ moles/cm$^2$ and the dose of hydrogen was $9\times10^{-7}$ moles/cm$^2$. The exposure of the substrates to the cobalt precursor was $1\times10^5$ Langmuirs/cycle and their exposure to hydrogen was $2\times10^7$ Langmuirs/cycle.

Figure 5:
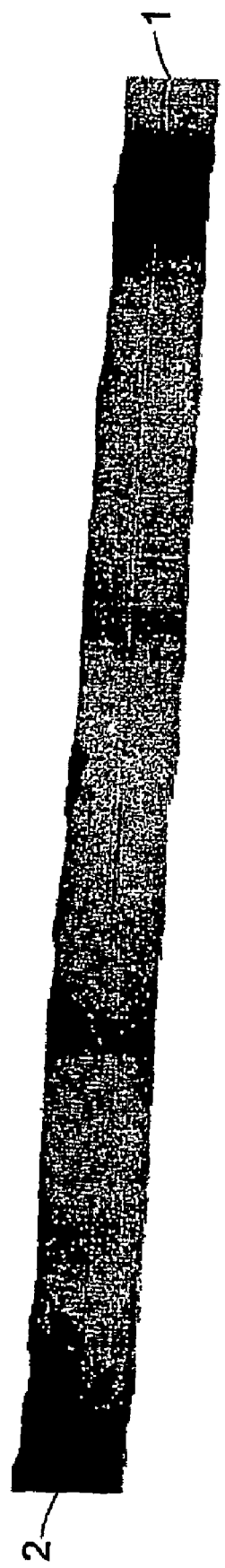
FIG. 5 is an optical micrograph of a narrow hole whose walls are coated with cobalt metal using one embodiment of the invention.

The substrates were examined by Rutherford Backscattering Spectroscopy and found to have a film of pure cobalt metal, $5\times10^{16}$ atoms/cm$^2$ thick or $8\times10^{-8}$ moles/cm$^2$ thick. The coated fused silica capillary was examined by optical microscopy, which showed that the cobalt film extended to at least 60 diameters (i.e. an aspect ratio >60) into the hole in the tubing. In FIG. 5, 1 points to the open end of the hole, and 2 shows how far the coating penetrated into the hole. This result demonstrates the excellent step coverage achieved by this process for ALD of cobalt.

Example 19

Figure 7:
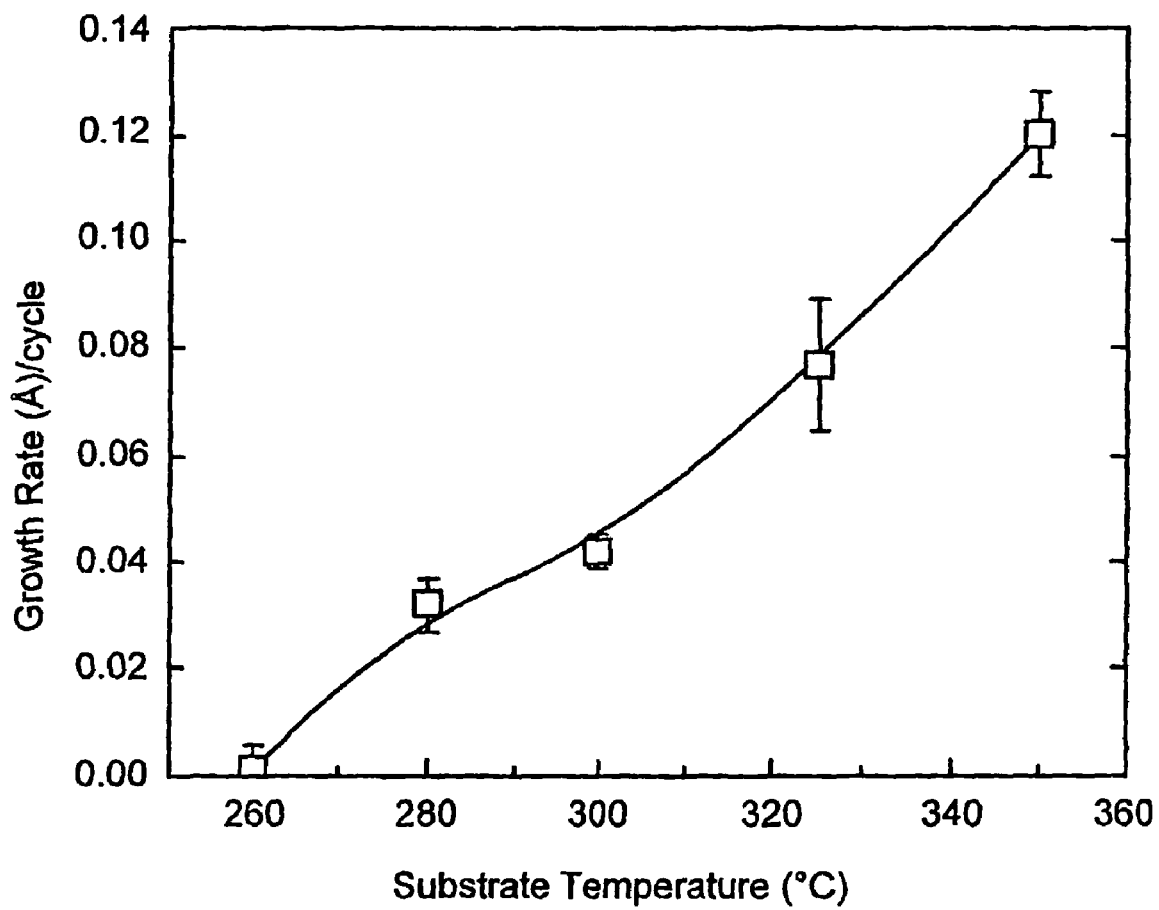
FIG. 7 is a plot of the thickness of cobalt deposited in each ALD cycle, as a function of substrate temperature.

Demonstration of a Range of Temperatures for Atomic Layer Deposition of Cobalt Example 18 was repeated, except that the substrate temperature was varied between 250 and 350° C. Similar results were obtained, except that the thickness per cycle varied with temperature as shown in FIG. 7. At substrate temperatures below 250° C., no deposition of cobalt was observed. This observation shows that walls of a reaction chamber remain free of unwanted cobalt deposits if the wall temperature is kept below 250° C. and above the dew point of the precursor.

Example 20

Atomic Layer Deposition of an Adherent Copper Film on a Co/WN Glue Layer/Diffusion Barrier The processes in Example 14 and Example 18 were repeated one after the other on a tungsten nitride (WN) layer previously coated onto silicon dioxide, WN/SiO$_2$/Si. A smooth, adherent film with the multi-layer structure Cu/Co/WN/SiO$_2$ was obtained. Adhesive tape was then applied to the surface of this multi-layer structure. No loss of adhesion was observed when the tape was pulled off.

Example 21

Atomic Layer Deposition of Cobalt Oxide

Example 18 was repeated, except that the hydrogen gas was replaced with water vapor. A uniform, smooth layer of cobalt oxide with composition approximately CoO was deposited.

Example 22

Atomic Layer Deposition of Metallic Nickel

Example 14 was repeated, except that nickel bis(N,N'-diisopropylacetamidinate) kept at 75° C. was used in place of the copper precursor and the substrate temperature was raised to 280° C. A silicon substrate previously coated with silicon dioxide and then with tungsten nitride was placed in the deposition chamber. In each cycle, the dose of nickel precursor was $4\times10^{-9}$ moles/cm$^2$ and the dose of hydrogen was $8\times10^{-7}$ moles/cm$^2$. The exposure of the substrates to the nickel precursor was $3\times10^4$ Langmuirs/cycle and their exposure to hydrogen was $7\times10^6$ Langmuirs/cycle.

The substrates were examined by Rutherford Backscattering Spectroscopy and found to have a film of pure nickel metal, $5\times10^{16}$ atoms/cm$^2$ thick or $8\times10^{-8}$ moles/cm$^2$ thick.

Example 23

Atomic Layer Deposition of Metallic Iron

Example 14 was repeated, except that iron bis(N,N'-di-tert-butylacetimidinate) kept at 75° C. was used in place of the copper precursor and the substrate temperature was raised to 280° C. A silicon substrate previously coated with silicon dioxide and then with tungsten nitride was placed in the deposition chamber. In each cycle, the dose of iron precursor was $4\times10^{-9}$ moles/cm$^2$ and the dose of hydrogen was $4\times10^{-6}$ moles/cm$^2$. The exposure of the substrates to the iron precursor was $8\times10^4$ Langmuirs/cycle and their exposure to hydrogen was $4\times10^7$ Langmuirs/cycle.

The substrates were examined by Rutherford Backscattering Spectroscopy and found to have a film of pure iron metal, $5\times10^{16}$ atoms/cm$^2$ thick or $8\times10^{-8}$ moles/cm$^2$ thick.

Example 24

ALD of Iron Oxide

Example 21 was repeated, with bis(N,N'-di-tert-butylacetamidinato)iron ([Fe($^t$Bu-AMD)$_2$]) kept at 85° C. in place of cobalt bis(N,N''-diisopropylacetamidinate). In each cycle, the dose of iron precursor was $4\times10^{-9}$ moles/cm$^2$ and the dose of water vapor was $8\times10^{-8}$ moles/cm$^2$. The exposure of the substrates to the iron precursor was $8\times10^4$ Langmuirs/cycle and their exposure to water vapor was $7\times10^5$ Langmuirs/cycle. A uniform, smooth layer of iron oxide with composition approximately FeO was deposited on substrates heated to 250° C.

Example 25

ALD of Lanthanum Oxide

Example 21 was repeated, with tris(N,N'-diisopropylacetamidinato)lanthanum ([La($^i$Pr-AMD)$_3$]) kept at 120° C. in place of cobalt bis(N,N'-diisopropylacetamidinate). In each of 50 cycles, the dose of lanthanum precursor was $4\times10^{-9}$ moles/cm$^2$ and the dose of water vapor was $8\times10^{-8}$ moles/cm$^2$. The exposure of the substrates to the lanthanum precursor was $3\times10^4$ Langmuirs/cycle and their exposure to water vapor was $7\times10^5$ Langmuirs/cycle. A uniform, smooth layer of lanthanum oxide about 5 nm thick, with composition approximately La$_2$O$_3$, was deposited on substrates heated to 300° C.

When the procedure of Example 21 was repeated with more than 50 cycles, the thickness was not uniformly distributed over samples in different parts of the reaction chamber, and the thickness per cycle was larger than 0.1 nm per cycle, particularly in the region near the exhaust to the vacuum pump. It is our interpretation of this effect that water vapor was absorbed into the bulk of the thicker lanthanum oxide layer during the water dose. During the few seconds of purge time following the water pulse some, but not all, of the adsorbed water was released back into the nitrogen gas and carried out of the chamber. However, further release of water vapor continued during the next dose of lanthanum precursor. Chemical vapor deposition of La$_2$O$_3$ then resulted from the reaction of this residual water vapor with the lanthanum precursor, yielding a larger than expected growth rate, particularly in the part of the deposition chamber closest to the exhaust to the vacuum pump. Uniform thickness could be restored by lengthening the purge time for the water vapor. A more practical solution for restoring the thickness uniformity is described in Example 26.

Example 26

ALD of Lanthanum Oxide/Aluminum Oxide Nanolaminate

Example 25 was repeated to deposit 16 cycles of lanthanum oxide. Then 6 cycles of aluminum oxide were deposited by ALD using alternating doses of trimethylaluminum vapor and water vapor, according to a process well-known in the art. This pattern of (16 La$_2$O$_3$+6 Al$_2$O$_3$) cycles was repeated 5 times. A uniform, smooth layer about 10 nm thick was deposited on substrates heated to 300° G. The layers had average composition approximately LaAlO$_3$. Capacitors made of this material had a dielectric constant about 18 and very low leakage current of about $5\times10^{-8}$ amperes per square centimeter at an applied potential of 1 volt.

Our interpretation of the thickness uniformity achieved in Example 26 is that the aluminum oxide layers act as a barrier to diffusion of water into the lower layers of lanthanum oxide.

Example 27

ALD of Manganese Oxide

Example 21 was repeated, with bis(N,N'-terf-butylacetamidinato)manganese ([Mn($^t$Bu-AMD)$_2$]) kept at 75° C. in place of cobalt bis(N,N'-diisopropylacetamidinate). In each cycle, the dose of manganese precursor was $4\times10^{-9}$ moles/cm$^2$ and the dose of water vapor was $8\times10^{-8}$ moles/cm$^2$. The exposure of the substrates to the manganese precursor was $3\times10^4$ Langmuirs/cycle and their exposure to water vapor was $6\times10^5$ Langmuirs/cycle. A uniform, smooth layer of manganese(II) oxide with composition approximately MnO was deposited on substrates heated to 250° C. at a deposition rate of about 0.1 nanometer per cycle.

Example 28

ALD of Magnesium Oxide

Example 21 was repeated, with bis(N,N'-tert-butylacetamidinato)magnesium ([Mg($^t$Bu-AMD)$_2$]), prepared by a procedure similar to that described in Example 3, kept at 80° C. in place of the cobalt bis(N,N'-diisopropylacetamidinate) used in Example 21. In each cycle, the dose of magnesium precursor was $3\times10^{-9}$ moles/cm$^2$ and the dose of water vapor was $6\times10^{-8}$ moles/cm$^2$. The exposure of the substrates to the magnesium precursor was $3\times10^4$ Langmuirs/cycle and their exposure to water vapor was $5\times10^5$ Langmuirs/cycle. A uniform, smooth layer of magnesium oxide with composition approximately MgO was deposited on substrates heated to 250° C. at a deposition rate of 0.08 nanometer per cycle.

Example 29

Synthesis of lithium N,N'-di-sec-butylacetamidinate

One equivalent of dry sec-butylamine, one equivalent of dry acetonitrile and 0.02 equivalents of lanthanum triflate, a catalyst, were placed into a Schlenk flask with a reflux condenser. Dry nitrogen was passed slowly into the flask, up through a reflux column and out of an oil bubbler while the reaction mixture refluxed for 3 days. Excess reactants were then removed under vacuum and the remaining liquid was purified by distillation to sec-butylacetamidine. $^1$H NMR (C$_6$D$_6$, 25° C.): 81.49 (m, 4H), 81.38 (s, 3H), 81.11 (d, J=6 Hz, 6H), 80.90 (t, J=8 Hz, 6H).

An ether solution of sec-butylacetamidine was prepared at a concentration of 1 gram per 10 ml of dry ether in a reaction flask with a reflux column and an oil bubbler. One equivalent of methyl lithium solution in ether was then added slowly to the sec-butylacetamidine solution and the reaction mixture was stirred for an hour. The resulting solution of lithium N,N'-di-sec-butylacetamidinate was then used without further purification for the synthesis of other metal .sec-butylacetamidinate salts. $^1$H NMR (C$_6$D$_6$, 25° C.) for lithium N,N'-di-sec-butylacetamidinate: 83.16 (m, 2H), 81.71 (s, 3H), 81.68 (m, 2H), 81.52 (m, 2H), 81.19 (d, J=6 Hz, 4H), 80.94 (m, 6H).

Example 30

Synthesis of cobalt bis(N,N'-di-sec-butylacetamidinate) ([Co(sec-Bu-AMD)$_2$])

Anhydrous cobalt(II) chloride, CoCl$_2$, was weighed into a Schlenk flask in a dry box. Two equivalents of the lithium N,N'-di-sec-butylacetamidinate solution prepared in Example 29 are added, along with an equal volume of dry THF. The reaction mixture was stirred overnight, and then the volatiles were removed under vacuum at room temperature. The solid was dissolved in dry hexanes, filtered, and the hexanes removed from the filtrate under vacuum at room temperature to give a crude yield of 82% of cobalt bis(N,N'-di-sec-butylacetamidinate). This liquid was purified by distillation (55° C. at 60 mtorr).

Example 31

Synthesis of copper(I) N,N'-di-sec-butylacetamidinate dimer ([Cu(sec-Bu-AMD)]$_2$)

The procedure of Example 30 was used with one equivalent of copper (I) chloride, CuCl, in place of the cobalt chloride and one equivalent of the lithium N,N'-di-sec-butylacetamidinate prepared in Example 29. [Cu(sec-Bu-AMD)]2 was isolated by the procedure of Example 30. Sublimation: 55° C. at 50 mtorr. mp. 77° C. [Cu(sec-Bu-AMD)]$_2$ has an advantage as a precursor for ALD of copper in that it is a liquid at the temperature used for vaporization (about 100° C.), resulting in more reproducible delivery of vapor than was obtained by sublimation of solid precursors.

Example 32

Synthesis of Bismuth tris(N,N'-di-tert-butylacetamidinate)dimmer ([Bi($^t$Bu-AMD)$_3$]$_2$)

One equivalent of bismuth trichloride, BiCl$_3$, and three equivalents of lithium N,N'-di-tert-butylacetamidinate (obtained by reaction of 1,3-di-tert-butylcarbodiimide with methyllithium) were refluxed overnight in THF. After the evaporation of the THF, extraction in dry hexanes, filtration and evaporation of the hexanes from the filtrate, the crude product was isolated by sublimation (70° C. at 80 mtorr). m.p.: 95° C. Dimeric by cryoscopy in p-xylene solution.

Example 33

Synthesis of Strontium bis(N,N'-di-tert-butylacetamidinate) ([Sr($^t$Bu-AMD)$_2$)$_n$)

Following a procedure similar to that used in Example 32, strontium bis(N,N'-di-tert-butylacetamidinate) was obtained. The crude product was purified by sublimation (130° C. at 90 mtorr).

Example 34

ALD of Bismuth Oxide, Bi$_2$O$_3$

Following a procedure similar to Example 25, films of bismuth oxide, Bi$_2$O$_3$, were deposited on substrates at a temperature of 200° C. from a vapor source containing bismuth tris(N,N'-di-tert-butylacetamidinate) at 85° C. The thickness of the films was about 0.03 nanometers per cycle.

Example 35

Synthesis of tris(N,N'-diisopropylacetamidinato) ruthenium ([Ru($^i$Pr-AMD)$_3$])

Following a procedure similar to Example 11, tris(N,N'-diisopropylacetamidinato)-ruthenium ([Ru($^i$Pr-AMD)$_3$]) was obtained in low yield.

Comparative Example 1

Example 14 was repeated using only the copper precursor, and no hydrogen gas. No film was observed to have been deposited on the substrate surface.

Comparative Example 2

Example 18 was repeated using only the cobalt precursor, and no hydrogen. No film was observed to have been deposited on the substrate surface.

Those skilled in the art will recognize or be able to ascertain using no more than routine experimentation, many equivalents to the specific embodiments of the invention described specifically herein. Such equivalents are intended to be encompassed within the scope of the following claims.

What is claimed is:

1. A compound represented by the general formula

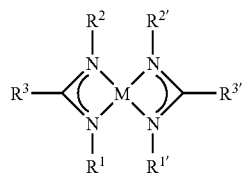

or oligomers thereof, wherein the metal M is selected from the group consisting of cobalt, nickel, ruthenium, zinc, titanium, europium, strontium, and calcium, and wherein $R^1$, $R^{1'}$, $R^2$, and $R^{2'}$ independently represent alkyl groups, alkenyl groups, alkynyl groups, trialkylsilyl groups, or other non-metal atoms or groups that are not aryl, and $R^3$ and $R^{3'}$ independently represent hydrogen, alkyl groups, alkenyl groups, alkynyl groups, trialkylsilyl groups, or other non-metal atoms or groups that are not aryl.

2. The compound as claimed in claim 1, wherein $R^1$, $R^{1'}$, $R^2$, $R^{2'}$, $R^3$ represent alkyl groups substituted with fluorine or other non-metal atoms.

3. The compound as claimed in claim 1, wherein $R^1$, $R^{1'}$, $R^2$, $R^{2'}$, $R^3$ and $R^{3'}$ represent unsubstituted alkyl groups.

4. The compound as claimed in claim 1, wherein M is cobalt.

5. The compound as claimed in claim 1, wherein M is nickel.

6. The compound as claimed in claim 1, wherein M is ruthenium.

7. The compound as claimed in claim 1, wherein M is strontium.

8. The compound as claimed in claim 1, wherein $R^1$, $R^{1'}$, $R^2$, and $R^{2'}$ are all tertiary butyl groups, $R^3$ and $R^{3'}$ are both methyl groups, and M is calcium or strontium.

9. The compound as claimed in claim 1, wherein $R^1$, $R^{1'}$, $R^2$, and $R^{2'}$ independently represent alkyl groups, alkenyl groups, alkynyl groups, or trialkylsilyl groups, and $R^3$ and $R^{3'}$ independently represent hydrogen, alkyl groups, alkenyl groups, alkynyl groups, or trialkylsilyl groups.

10. A compound represented by the general formula

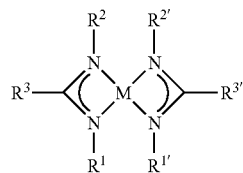

or oligomers thereof, wherein M is iron, manganese, or magnesium and $R^1$, $R^{1'}$, $R^2$, and $R^{2'}$ independently represent alkyl groups, alkenyl groups, alkynyl groups, trialkylsilyl groups, or other non-metal atoms or groups that are not aryl, and $R^3$ and $R^{3'}$ independently represent hydrogen, alkyl groups, alkenyl groups, alkynyl groups, trialkylsilyl groups, or other non-metal atoms or groups that are not aryl, but excluding the compounds [$^t$BuC(N$^i$Pr)$_2$]$_2$Fe, [$^t$BuC(N-cyclohexyl)$_2$]$_2$Fe, [MeC(N$^i$Pr)$_2$]$_2$Mg, [MeC(N$^t$Bu)$_2$]$_2$Mg, [MeC(NEt)(N$^t$Bu)]$_2$Mg, and [HC(N-cyclohexyl)$_2$]$_2$Mn.

11. The compound of claim 10, wherein $R^1$, $R^{1'}$, $R^2$, and $R^{2'}$ independently represent alkyl groups, alkenyl groups, alkynyl groups, or trialkylsilyl groups, and $R^3$ and $R^{3'}$ independently represent hydrogen, alkyl groups, alkenyl groups, alkynyl groups, or trialkylsilyl groups.

12. A process for depositing a material comprising a metal, M, the process comprising exposing a vapor of a first reagent to a substrate, followed by exposing a second reagent vapor to the substrate, wherein the first reagent comprises a compound represented by the general formula

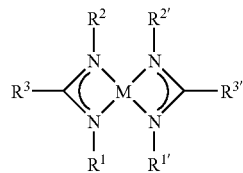

or oligomers thereof, wherein $R^1$, $R^{1'}$, $R^2$, and $R^{2'}$ independently represent alkyl groups, aryl groups, alkenyl groups, alkynyl groups, trialkylsilyl groups, or other non-metal atoms or groups, and $R^3$ and $R^{3'}$ independently represent hydrogen, alkyl groups, aryl groups, alkenyl groups, alkynyl groups, trialkylsilyl groups, or other non-metal atoms or groups.

13. The process of claim 12, wherein the second reagent is a reducing gas or vapor.

14. The process of claim 13, wherein the reducing gas is hydrogen.

15. The process of claim 12, wherein the second reagent is a nitrogen-containing gas.

16. The process of claim 15, wherein the nitrogen-containing gas is ammonia.

17. The process of claim 12, wherein the second reagent is an oxygen-containing gas.

18. The process of claim 17, wherein the second reagent is water.

19. The process of claim 12, wherein $R^1$, $R^{1'}$, $R^2$, and $R^{2'}$ independently represent alkyl groups, aryl groups, alkenyl groups, alkynyl groups, or trialkylsilyl groups, and $R^3$ and $R^{3'}$ independently represent hydrogen, alkyl groups, aryl groups, alkenyl groups, alkynyl groups, or trialkylsilyl groups.

20. A process for depositing a material comprising a metal, M, the process comprising exposing a vapor of a reagent to a substrate, wherein the reagent comprises a compound represented by the general formula

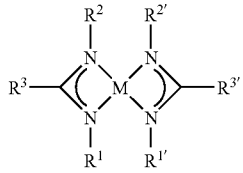

or oligomers thereof, wherein $R^1$, $R^{1'}$, $R^2$, and $R^{2'}$ independently represent alkyl groups, aryl groups, alkenyl groups, alkynyl groups, trialkylsilyl groups, or other non-metal atoms or groups, and $R^3$ and $R^{3'}$ independently represent hydrogen, alkyl groups, aryl groups, alkenyl groups, alkynyl groups, trialkylsilyl groups, or other non-metal atoms or groups, and wherein the metal M is not magnesium.

21. The process of claim 20, further comprising contacting the substrate with a reducing gas or vapor.

22. The process of claim 21, wherein the reducing gas is hydrogen.

23. The process of claim 20, further comprising contacting the substrate with a nitrogen-containing gas.

24. The process of claim 23, wherein the nitrogen-containing gas is ammonia.

25. The process of claim 20, further comprising contacting the substrate with an oxygen-containing gas.

26. The process of claim 25, wherein the oxygen-containing gas comprises water.

27. The process of claim 20, wherein $R^1$, $R^{1'}$, $R^2$, and $R^{2'}$ independently represent alkyl groups, aryl groups, alkenyl groups, alkynyl groups, or trialkylsilyl groups, and $R^3$ and $R^{3'}$ independently represent hydrogen, alkyl groups, aryl groups, alkenyl groups, alkynyl groups, or trialkylsilyl groups.

* * * * *

UNITED STATES PATENT AND TRADEMARK OFFICE
CERTIFICATE OF CORRECTION

PATENT NO. : 7,737,290 B2
APPLICATION NO. : 12/496499
DATED : June 15, 2010
INVENTOR(S) : Roy G. Gordon et al.

It is certified that error appears in the above-identified patent and that said Letters Patent is hereby corrected as shown below:

Title page, Item (73) Assignee's Name: "President and Fellows of Harvard University, Cambridge, MA (US)" should read -- President and Fellows of Harvard College, Cambridge, MA (US) --.

Signed and Sealed this

Thirtieth Day of November, 2010

David J. Kappos
*Director of the United States Patent and Trademark Office*

UNITED STATES PATENT AND TRADEMARK OFFICE
CERTIFICATE OF CORRECTION

PATENT NO.        : 7,737,290 B2
APPLICATION NO.   : 12/496499
DATED             : June 15, 2010
INVENTOR(S)       : Roy G. Gordon et al.

Page 1 of 1

It is certified that error appears in the above-identified patent and that said Letters Patent is hereby corrected as shown below:

In the Claims

Please replace the text beginning in column 21, line 47, "2. The compound as claimed in" to and ending with "non-metal atoms." in column 21, line 49, with the following:

--2. The compound as claimed in claim 1, wherein $R^1$, $R^{1'}$, $R^2$, $R^{2'}$, $R^3$ and $R^{3'}$ represent alkyl groups substituted with fluorine or other non-metal atoms.--

Signed and Sealed this
Twenty-sixth Day of November, 2013

Margaret A. Focarino
*Commissioner for Patents of the United States Patent and Trademark Office*